United States Patent [19]
Katinger et al.

[11] Patent Number: 5,739,021
[45] Date of Patent: Apr. 14, 1998

[54] HEAT-STERILIZABLE POROUS CARRIER FOR BIOCATALYSTS

[75] Inventors: Hermann Katinger, Vienna, Austria; Bartold Rauschert, Steinbach am Wald, Germany; Gerald Blüml, Vienna, Austria; Nicolaus Zach, Vienna, Austria; Manfred Reiter, Vienna, Austria; Theodor Gaida, Vienna, Austria

[73] Assignee: Pharmacia Biotech AB, Uppsala, Sweden

[21] Appl. No.: 390,768

[22] Filed: Dec. 28, 1994

Related U.S. Application Data

[63] Continuation-in-part of Ser. No. 980,806, filed as PCT/AT92/00081 Jul. 1, 1992, abandoned.

[30] Foreign Application Priority Data

Jul. 2, 1991 [AT] Austria ..................... 1322/91

[51] Int. Cl.$^6$ .................... C12N 11/08; C12N 5/04; C12N 5/02
[52] U.S. Cl. .................... 435/180; 435/182; 435/395; 435/403; 435/410
[58] Field of Search ............ 435/240.23, 240.24, 435/240.4, 240.48, 395, 403, 410, 180, 182

[56] References Cited

U.S. PATENT DOCUMENTS

| | | | |
|---|---|---|---|
| 4,076,656 | 2/1978 | White et al. | 521/64 |
| 4,144,126 | 3/1979 | Burbidge | 435/240.24 |
| 4,169,014 | 9/1979 | Goldberg | 435/182 |
| 4,246,350 | 1/1981 | Hier et al. | 435/180 |
| 4,987,068 | 1/1991 | Trösch et al. | 435/41 |
| 5,006,467 | 4/1991 | Kusano et al. | 435/180 |

FOREIGN PATENT DOCUMENTS 222 718 B1 11/1993 European Pat. Off. .

OTHER PUBLICATIONS

Billmeyer, Fred W., Jr., "Textbook of Polymer Science" (1984), pp. 471–472.

*Primary Examiner*—John W. Rollins
*Assistant Examiner*—Francisco C. Prats
*Attorney, Agent, or Firm*—Henry M. Feiereisen

[57] ABSTRACT

A porous carrier for biocatalysts (a) comprising a water-insoluble inorganic filler and a polyolefine binder selected from polyethylene and polypropylene, (b) having open pores allowing cells to penetrate and grow within its pores, and (c) having a density above 1 g/cm$^3$.

18 Claims, 5 Drawing Sheets

HEAT-STERILIZABLE POROUS CARRIER FOR BIOCATALYSTS

CROSS-REFERENCES TO RELATED APPLICATIONS

This is a continuation in part application from U.S. patent application Ser. No. 07/980,806 filed Mar. 30, 1993, now abandoned, which is a 371 of International Patent Application PCT/AT92/00081 filed Jul. 1, 1992.

TECHNICAL FIELD

The invention refers to heat-sterilizable porous carriers with large open pore volume.

The carriers are useful as support for biocatalysts in bioreactor systems, and in particular for the cultivation of cells, for instance micro-organisms and adherent and non-adherent mammalian cells. The bioreactor systems may be of the stirred, packed or fluidized bed type.

PRIOR ART CARRIERS

Some carrier types are already known for in-vitro culture of micro-organisms as well as animal cells. For cultivating mammalian cells, Cytodex® (Pharmacia Biotech AB, Sweden) is generally used. It is a carrier of spherical bead type (microcarriers). It is not porous and thus have the drawback of being suitable only for strictly adherent cells. Moreover, the maximal attainable cell densities for these prior art carriers are $10^7$ cells per ml.

Further there is known a porous carrier based on gelatine, which is suitable for bioreactors containing moveable substrates. Likewise, U.S. Pat. No. 4,863,856 discloses a carrier made of collagen. Common to both the collagen and the gelatine type of carriers is that they are made up of material of animal nature. Such material is heterogeneous so that uniform quality and properties can rarely be obtained. Contamination risks of viruses, virus like particles, or bovine spongioform enzephalitis (BSE) are also at hand. Therefore, the quality control becomes complicated. Moreover, these materials can not be satisfactorily heat sterilized.

Other carriers for cell culturing have been described previously:

U.S. Pat. No. 5,006,467 gives cell culture microcarriers that are essentially non-porous with a density of 1.00–1.20 g/ml and a size of 100–1000μ. The presence of fillers appears to be non-essential. The base polymers are different cross-linked forms of polyethylene glycol poly(meth) acrylate esters.

U.S. Pat. No. 4,144,126 describes a flow through system with a porous support. The support may be an integral matrix or packed dense beads or fibres with the interstices between the particles forming the pore system. The density of the support seems to be of minor importance because there exist various simple ways of keeping the bed support in place.

There is also known heat-sterilizable porous carriers in which the carrier is built up by porous sintered glass (Siran®, Scott). These carriers are mainly used in packed bed reactors which are characterized by a stationary bed and thus by the absence of relative movement between individual carrier particles. In fluidized bed reactors and stirred reactors, the sintered glass carriers are only usable in a limited fashion because the relative movement of the particles causes an abrasion which is damaging to the animal cells being cultivated. Moreover the sintered glass carriers may lose their desired structure as their surfaces are subjected to mechanical influences.

During the time period between the filing dates of the parent priority application and the present application a macroporous microcarrier initially named Polypore (later renamed to Cytoline) become commercially available (Collaborative Biotech GmbH, Vienna Austria). The first versions of these microcarriers had a high density polyethylene (HDPE) as the binder and were weighted by inclusion of chalk. Later chalk was replaced by an aluminosilicate (MICA G from Aspanger AG, Aspang, Austria). Results with these carriers without reference to their method of production have been published Blüml et al., (1992) In. Animal Cell Technology: Developments, Processes and Products (Eds. Spier, Griffiths and MacDonald), 501–504, Butterworth-Heinemann Ltd, Oxford, UK}.

Integral materials, in particular in sheet/membrane forms, have been used as support for enzymes in bioreactors. For example, U.S. Pat. No. 4,169,014 describes a microporous membrane (pore size 0.01–100μ, pore volume typically within 50–70%) built up by a polymeric base and conventional fillers. Polyvinyl chloride is given as an example of a base polymer.

Further, U.S. Pat. No. 4,076,656 describes membranes of undefined porosity that in some cases can be used as supports for enzymes and catalysts. These membranes comprise a base polymer that optionally may contain a filler. During their manufacture, hole forming and channeling agents are compounded with a base polymer. Low density to high density polyethylenes and polyvinyl methyl ethers are given as examples of base polymers and channeling agents, respectively.

The density of membranes to be used in bioreactors are of minor importance because membranes normally are fixedly mounted so that a defined flow of liquid can pass through them.

U.S. Pat. No. 4,246,350 describes supports for immobilization of proteins via immobilized metal chelates. The support may be in beaded form and the only specific type of base polymers given is styrendivinylbenzene copolymers. The specification says that the supports are microporous and the pore sizes given are extremely small (0.005–0.2μ).

OBJECTS OF THE INVENTION

It is an object of the invention to create carriers that can be used for different types of bioreactors (e.g. stirred, fluidized and fixed bed reactors), and then in particular for the cultivation of the cells. A particular object is to provide heat sterilizable carriers. Accordingly one object of the invention is to provide an improved method of culturing cells on porous carriers. See below.

THE INVENTION

These objects are attained in accordance with the invention by providing a carrier material with large open pores and containing a polyolefine as the base polymer (binder) together with a filler. In a preferred general embodiment the carrier consists essentially of filler and polyolefine.

The open pores are within the range of 1–400μ, such as 1–300μ, with an open pore volume between 60–85% of the carrier material. This does not exclude that there may be present also pores outside this interval. The pore structure of the carriers may be open by 50–60%, such as 50–80%, which in turn provides a very high specific effective surface. During cell cultivation, the cells are retained (immobilized) in the porous structure of the carriers to thereby allow the production of very high cell densities.

In case the carrier material is in the form of particles these are within the size range of 0.1–2.5 mm, such as 0.1–2.0 mm. The carrier particles in a preferred embodiment have a lenticular shape with a length that may be 1.7–2.5. In order to achieve the most optimal diffusion of nutrients and oxygen inside the carrier particles the distance from essentially all interior porous parts to the surface of the particles should be less 0.5 mm. These features mean that for lenticular carriers the preferred size with respect to thickness is within the range of 0.4–1.1 mm, such as 0.5–1 mm.

The density is preferably greater than 1 g/cm$^3$. The speed of descent (sedimentation velocity) for particulate carriers contemplated for fluidized bed reactors may in many cases amounts to about 80–250 cm/min, such as 150–170 cm/min. For stirred tank fermentors/reactors, the density of the particulate carriers may be set slightly lower which also indicates a lower sedimentation velocity than carriers contemplated for fluidized beds. In packed bed reactors, however, the particulate carriers should have a higher speed of descent and thus also a higher density. Accordingly, by incorporating the proper constituents in the inventive particulate carriers, the invention may be usable in every type of reactor, i.e. in stirred bioreactors, fluidized bed reactors, packed bed reactors and reactors utilizing integral carriers (for instance membranes).

Advantageously the polyolefine is a polyethylene such as high-density polyethylene (HDPE), a polypropylene or the like. High density and low density (that encompasses high pressure polyethylenes) are recognized concepts. See for instance Encyclopedia of Polymer Science and Engineering, Vol. 6, John Wiley & Sons (1986) 383–386. High density polyethylenes has a high ratio of crystallisation which is determined from the numbers of side chains. The increase in crystallisation of polyethylenes increases the melting temperature, rigidity and resistance against chemical solvents and make HDPEs polypropylenes suitable as binders (base polymers) in carriers that have to be treated under harsh conditions. Further, in view of the spectrum of physical properties that can be obtained with different polymer materials and filler combinations, carriers adapted for a wide range of cells, such as different micro-organisms, and especially different adherent and non-adherent mammalian cells as well as plant cells, are provided according to the invention.

By selecting the proper polyolefinic base polymer, for instance a high density polyethylene or high density polypropylene, autoclaving becomes possible, i.e. heat sterilization of the carrier material, e.g. by heating to a sufficient temperature and for a sufficient time to kill contaminating living material. High density polyethylenes allow sterilization up to 121° C., above which the pores becomes deformed. Polypropylenes may allow higher temperatures but may have disadvantages (see below). The sterilization time is often around 30 min, with 20 minutes being a minimum. This means that the complete culturing unit comprising the present inventive carriers can be sterilized before inoculating with the cells to be cultivated.

The filler may be of inorganic nature (inorganic salt), such as a heavy metal salt, chalk or silicate, or other suitable fillers. It is a matter of course that the filler, for instance a heavy metal salt filler, has to be insoluble in the fluid that is to be contacted with the carrier. Likewise, in case cells are to be cultured in the porous carrier material of the invention, the heavy metal salt fillers used also have to be non-toxic for said cells.

The charge of ions, such as $Ca^{2+}$, also affords an ion exchange capacity onto the carriers, which positively should affect the growth of cells (including micro-organisms) and the mass transfer of nutrient substrate and immobilization of biocatalysts directly on the surface of the carriers. Chalk, and then its $Ca^{2+}$ ions, may be very favourable for the adherence of cells but then only in contact with fluids having a pH above about 6. In cell cultivation, for instance, it is known that the formation of an extra cellular matrix is promoted by calcium-ions (Ruoslahti and Pierschbacher, Science 238 (1987) 491; Pytela et al., Methods Enzymol. 144 (1987) 475; Chakravarti et al., J. Biol. Chem. 265 (1990) 10597.

To date the most preferred filler group is the silicates, and then particularly negatively charged silicates in which a defined amount of $Si^{4+}$-ions are replaced by metal ions of lower charge, such as $Al^{3+}$ (aluminosilicates). Negatively charged silicates may be illustrated by those in which 10–40% of $Si^{4+}$ has been replaced, for instance MICA G (Aspanger AG, A-2870 Aspang, Austria) in which the replacement number is 25% and the substituting ion is $Al^{3+}$. See also Ullmanns Encyklopädie der technischen Chemie, 4 ed. (1982) Volume 21, Silicate, Glimmer pp 400–403, Verlag Chemie.

By selecting different combinations of fillers and base polymers, carriers of different densities can be manufactured. The ratio of filler to polyolefine, in particular polyethylene (such as HDPE), may range from 1:1 to 1:10, such as from 1:1.5 to 1:4.5 (w/w). The specific combination is determined by the intended use with a representative ratio being 1:3. Fluidized bed and packed bed applications may require heavier carriers and consequently higher relative amounts of filler, for instance the filler to base polymer ratio can then be around 1:1 to 1:2, such as 1:1.4. For stirred bed reactors and fluidized beds with sensitive cells the carriers may be lighter, and the filler to base polymer (binder) ratio may then range from 1:3 to 1:10. These ranges are particularly adapted for chalk, silicates and other fillers of similar densities.

The carrier according to the invention is typically made by blending (compounding) the polymer material with water-insoluble and water-soluble inorganic materials (fillers and pore forming agents, respectively). The blend is extruded and the water-soluble inorganic components subsequently extracted thereby giving an open porous polymer matrix (carrier particles). The pore size is a function of the particle size of the water-soluble inorganic component used. Alternative methods and modifications thereof known in the prior art exist. See for instance the previous cited publications. Formation of open pores runs quite well with polyethylenes. For polypropylenes pore formation may be hindered since this latter binder has a tendency to form matrixes in which the grains of the water-soluble salt are fully engulfed by the binder rendering their dissolution difficult during the extraction step.

The soluble inorganic substance blended with the base polymer and filler amounts to 30–85%, such as 50–70% (w/w) of the blend and with a graining of 1–400μ, such as 1–300μ. Examples of preferred soluble substances are $Cl^-$ and $SO_4^{2-}$ salts, in particular corresponding alkali salts and alkaline earth salts, e.g. potassium chloride, sodium chloride, calcium sulfate. The soluble inorganic components may be substituted by blowing agents; however, upon use of blowing agents, it must be ensured that the final carrier has outwardly open pores. In case larger pores than 400μ are desired soluble salts having grains larger than 400μ are used.

As indicated above the main field of use of the present invention is for cell culturing. The specific conditions under which the inventive carriers are used are the same as normally contemplated with other carriers, i.e. the conditions to be used are more dependent on the cells to be cultivated than on the carriers used. For a general survey on different cells and cultivating requirements see Animal Cell Biotechnology. R. E. Spier and S. B. Griffiths (eds). Academic Press, volumes 1 (1985) and 2 (1988). Generic names for cells which can be cultivated on the present inventive carriers have been given above. By using the present carriers it now has become possible to sterilize the carriers by heating them at least up to 121° C. before inoculating them with the cells to be cultured.

BRIEF DESCRIPTION OF THE DRAWINGS

The attached drawings show the pore structure of the carrier and the flow behaviour of the bioreactor.

Figure 1A:
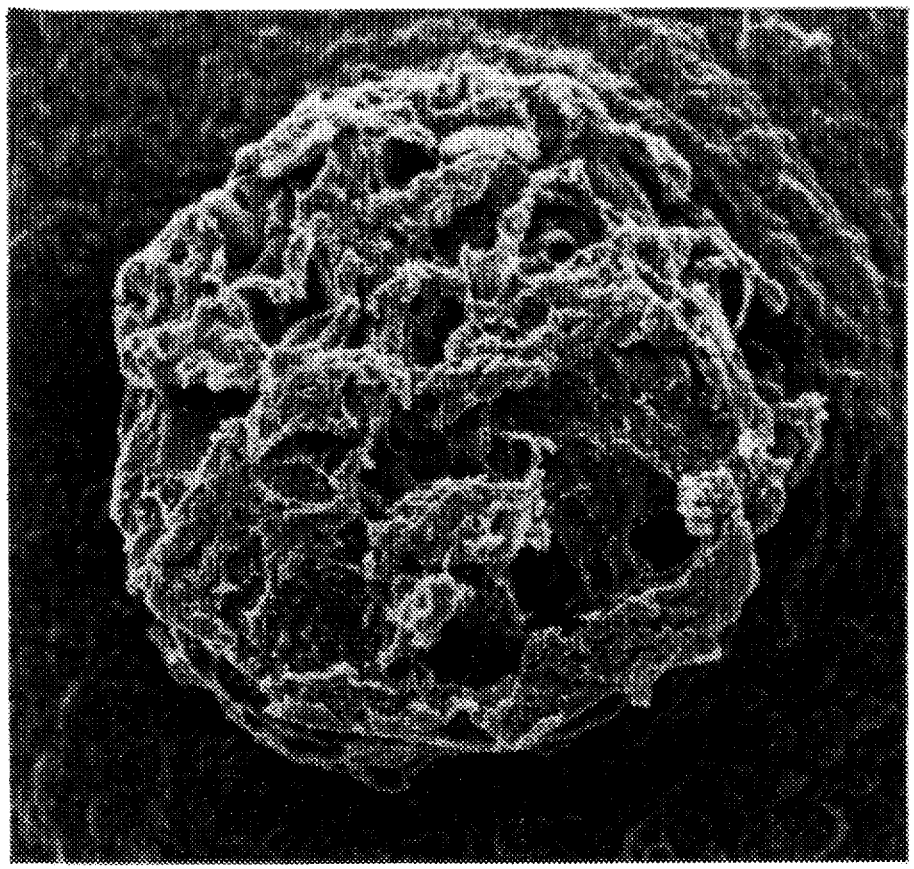
FIG. 1A shows the pore structure of the carrier.
Figure 1B:
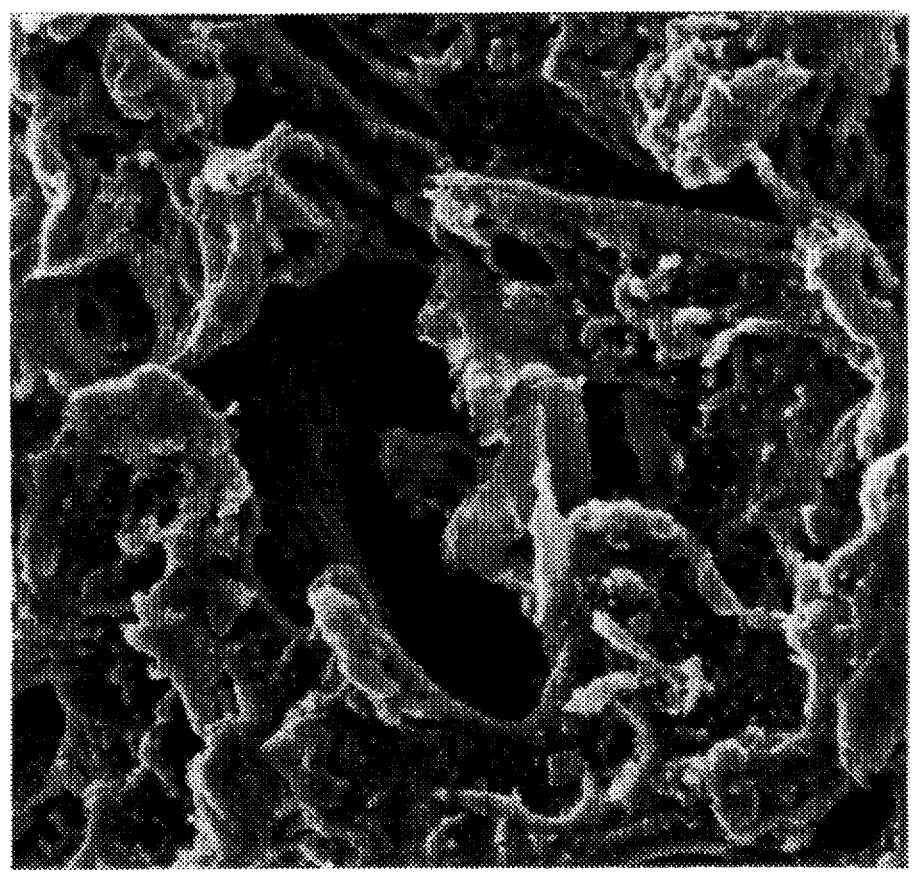
FIG. 1B shows the pore structure of the carrier in detail.
Figure 1C:
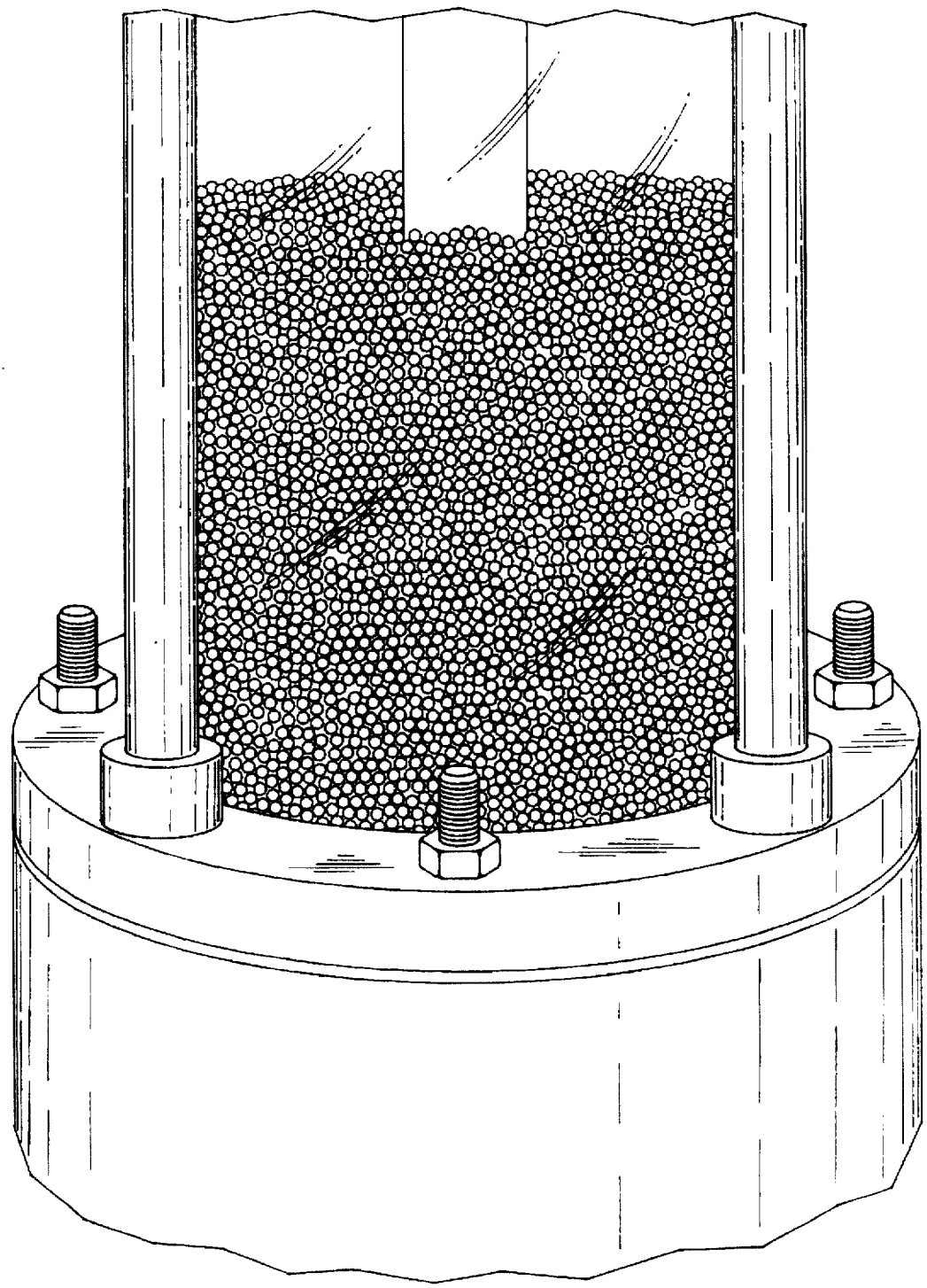
FIG. 1C shows the flow behaviour of a bioreactor containing the inventive carrier in particle form.
Figure 2A:
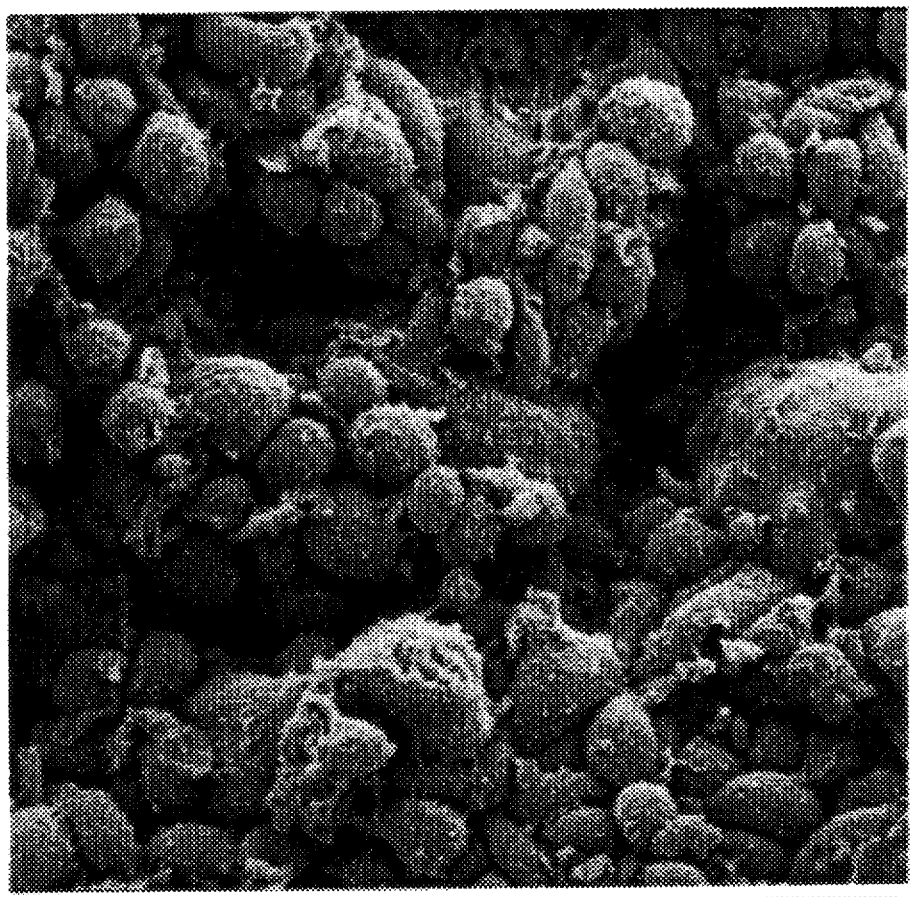
FIG. 2A shows adherent animal cell (CHO) which are cultivated on the inventive porous carrier.
Figure 2B:
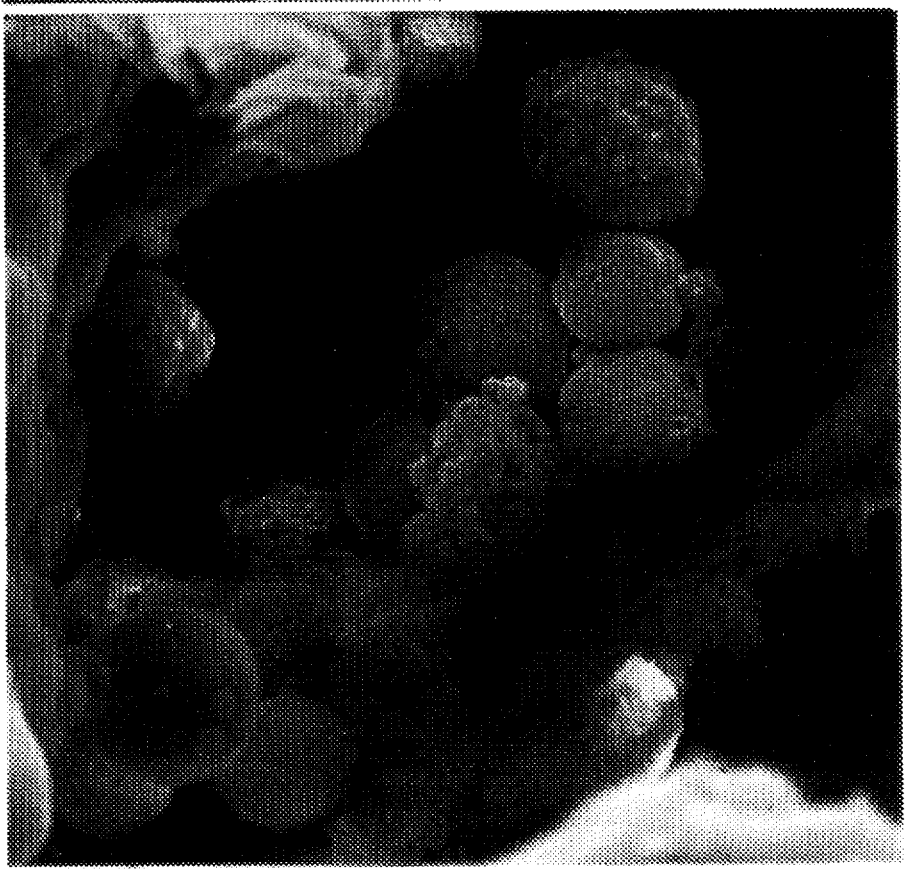
FIG. 2B shows suspension cells (hybridoma cells) cultivated in the presence of the inventive carrier.

In summary, it can be set forth that the advantages of the carrier according to the invention are:

Defined pore structure

Defined specific weight (results in ideal flow behaviour in stirred and fluidized bed reactors).

Mechanical resistance.

Resistance with regard to acids.

Resistance with regard to enzymatic degradation, thus long-term stability.

Toxic residues can be eliminated.

Suitable for se in stirred and non-stirred bioreactors.

Treatment by autoclaving at most up to 121° C.

Surface modification possible.

EXAMPLE 1

Manufacture of Carrier Material

The best mode carrier of the invention was at the priority date (Jul. 2, 1991) prepared according to the below recipe.

Materials: 50% soluble inorganic salt, grain size 0.1–0.3 mm; 12.5% chalk in powder form; 37.5% polyethylene (HDPE (Hostalen GC 7260 natur from Hoechst AG, Germany) with a density of 0.962 g/cm$^3$ and a melting index according to 190/2 that amounts to 6 g/10 min).

The plastic material (HDPE) is finely comminuted and a thorough mixture containing all three components is prepared. The mixture is then extruded by means of a synchronous double screw extruder at a pressure of about 300 bar and a processing temperature of about 180° C. The extrusion strand is cut by means of a granulator in a fog and the cut pellets are cooled in a water bath to wash out the salt (soluble inorganic material). In the next step, the pellets are dried in a centrifuge and, if necessary, autoclaved before used.

EXAMPLE 2

Manufacture of Carrier Material

The best mode of manufacturing the inventive carrier material at the filing date of this application (December, 1994) substitutes chalk with MICA G (Aspanger) which is a silicate in which one quarter of the Si-ions has been replaced by aluminium ions. Two illustrative recipes are:

| Material | w/w-% including salt | v/v-% | w/w-% washed carrier | v/v-% |
|---|---|---|---|---|
| CYTOLINE 1 | | | | |
| HDPE | 17.3 | 32.8 | 58.8 | 81 |
| MICA G | 12.1 | 7.7 | 41.2 | 19 |
| NaCl | 70.6 | 59.5 | | |
| Filler:HDPE | | | 1:1.4 | 1:4.3 |
| CYTOLINE 2 | | | | |
| HDPE | 26.4 | 48.4 | 89.8 | 96.2 |
| MICA G | 3 | 1.9 | 10.2 | 3.8 |
| NaCl | 70.6 | 49.7 | | |
| Filler:HDPE | | | 1:8.8 | 1:25.3 |

The HDPE quality was the same as in example 1.

Cytoline 1 results in a relatively heavy carrier that is best fitted for fluidized/expanded bed and packed bed applications. Cytoline 2 gives a lighter carrier that is more adapted for stirred systems and fluidized bed with sensitive cells.

All three components are mixed, warmed up under pressure in an extruder so that the polyethylene melts with a subsequent extrusion through a porous plate. The strings coming out from porous plate are cut under a water stream with rotating knives. The carrier particles so formed are transported under water to a separator and dryer. During the transportation the water-soluble salt (NaCl) is washed out. The ready-made carrier is collected after the dryer.

The carrier particles formed by this process have lens form structure. Normally the cutting is adjusted to give a length of about 2–2.5 mm of the particle. The thickness is determined by the pore size of the porous plate, normal values are 0.5–1.0 mm.

EXAMPLE 3

Cultivation of Different Cells

Different cells were tested for growth on the microcarriers prepared in examples 1 and 2. Before being inoculated with living cells, the carriers were sterilized by autoclaving at 121° C. The culturing conditions for the cells where the same as normally contemplated in connection with culturing on prior art carriers.

EXAMPLE 3a

Figure 3A:
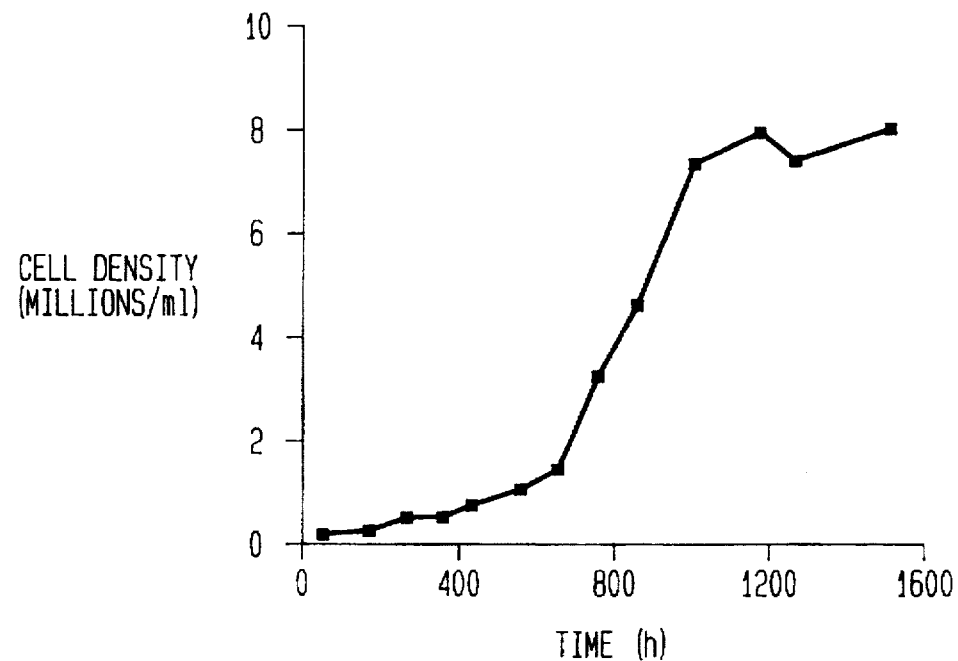
FIG. 3A–D show cell density, perfusion rate, productivity and glucose and lactate concentrations versus time for culturing of a recombinant CHO cell line on a chalk microcarrier in a fluidized bed.
Figure 3B:
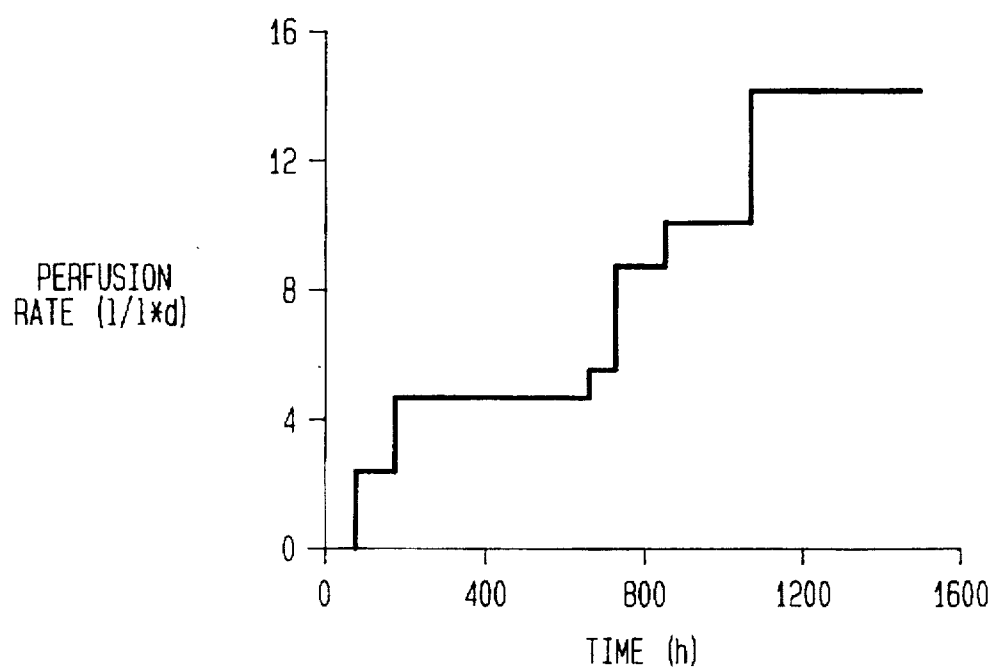
Figure 3C:
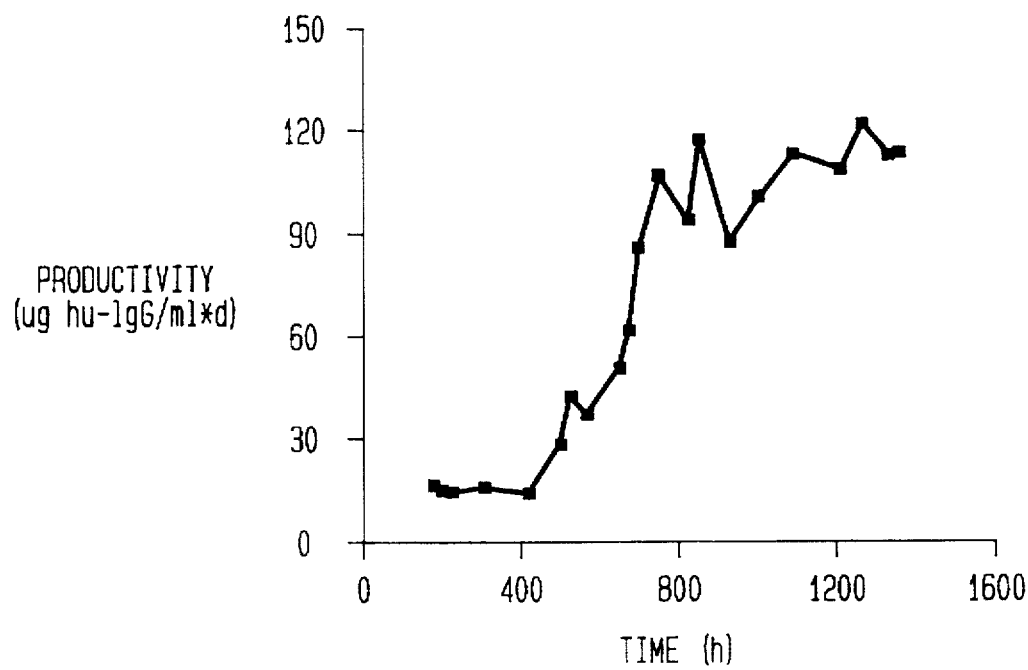
Figure 3D:
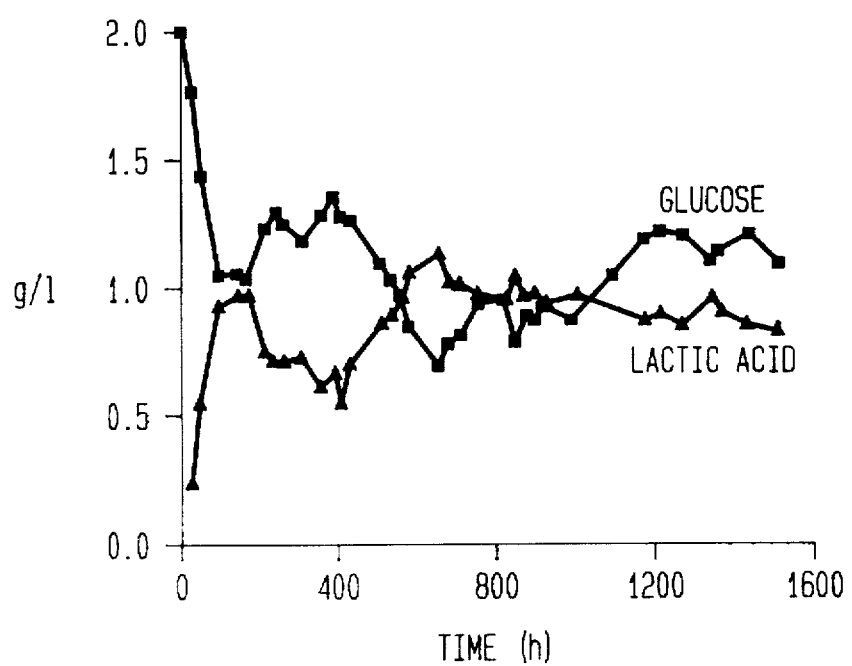

The microcarrier from example 1 (filler chalk). Growth and production kinetics of recombinant CHO cells (human monoclonal anti HIV 1 antibody) cultured on a chalk carrier in a fluidized bed are given in FIGS. 3A–D. FIG. 3A gives cell density versus time. FIG. 3B gives perfusion rate versus time. FIG. 3C gives productivity versus time. FIG. 3D gives concentration of glucose and lactate in the supernatant versus time.

EXAMPLE 3b

The following cell lines were grown on Cytoline 1 (fluidized bed) and Cytoline 2 (stirred reactor): CHO K1, recombinant CHO (5 different), BHK 21, r-BHK, murine fibroblasts, murine-hybridoma (4 different), human hybridoma (5 different), melanoma, Vero cells, insect cells, and nitrificant bacterias.

Comments: The average achieved cell densities were for r-CHO cell about $0.5 \times 10^8$ to $2.0 \times 10^8$ cells/ml (in media containing FCS as well as in protein free media); for human hybridoma up to $1.0 \times 10^7$ cells/ml (in media containing FCS); for murine hybridoma up to $2.0 \times 10^7$ cells/ml (in media containing FCS as well as in protein free media); and for murine fibroblasts about $0.5 \times 10^8$ to $2.0 \times 10^8$ cells/ml (in media containing FCS).

Many of the results given above have recently been published. See Lettner H P. (1993) Thesis at the institute of Applied Microbiology, University of Agriculture, Vienna, Austria; and Mosor T (1993), Diplom-work at the Institute of Applied Microbiology, University of Agriculture, Vienna, Austria.

We claim:

1. In a method for culturing cells on a carrier, the improvement comprising a carrier
   a) being in particle form exhibiting particles with outwardly open pores allowing the cells to penetrate and grow within the pores;
   b) having a density above 1 g/cm$^3$; and
   c) comprising a water-insoluble filler and a polyolefine binder selected from the group consisting of a high density polyethylene and a high density polypropylene, with said binder allowing heat sterilization of the carrier up to 121° C.

2. The method of claim 1 wherein the carrier particles have a size within the range of 0.1–2.5 mm.

3. The method of claim 1 wherein the particles have a lenticular shape with a distance from any interior pore to the surface being less than 0.5 mm.

4. The method of claim 1 wherein the binder is a high density polyethylene.

5. The method of claim 4 wherein the carrier particles have sizes within the range of 0.1–2.0 mm.

6. The method of claim 4 wherein the filler is chalk.

7. The method of claim 4 wherein the filler is silica.

8. The method of claim 7 wherein the filler is aluminosilicate.

9. The method of claim 4 wherein the particles have pores within the range of 1–300µ.

10. The method of claim 4 wherein the ratio filler to polyolefine is 1:1.5 to 1:4.5.

11. The method of claim 4 wherein the cells are selected from adherent mammalian cells.

12. The method of claim 4 wherein the cells are selected from non-adherent cells.

13. The method of claim 4 wherein the cells are selected from microorganisms.

14. The method of claim 1 wherein the filler is chalk.

15. The method of claim 1 wherein the filler is silica.

16. The method of claim 15 wherein the filler is aluminosilicate.

17. The method of claim 1 wherein the particles have pores within the range of 1–400µ.

18. The method of claim 1 wherein the ratio filler to polyolefine is 1:1 to 1:10.

* * * * *